United States Patent
Bak et al.

(10) Patent No.: US 8,362,342 B2
(45) Date of Patent: Jan. 29, 2013

(54) *TILLANDSIA* PLANT NAMED 'MORA'

(75) Inventors: Elly Bak, Rijsenhout (NL); Nicolaas D. M. Steur, Oude Niedorp (NL)

(73) Assignee: Corn.Bak B.V., Assendelft (NL)

( * ) Notice: Subject to any disclaimer, the term of this patent is extended or adjusted under 35 U.S.C. 154(b) by 309 days.

(21) Appl. No.: 12/923,861

(22) Filed: Oct. 12, 2010

(65) Prior Publication Data
US 2011/0209233 A1    Aug. 25, 2011

Related U.S. Application Data

(60) Provisional application No. 61/307,663, filed on Feb. 24, 2010.

(51) Int. Cl.
*A01H 1/00* (2006.01)
*A01H 5/00* (2006.01)
*A01H 5/10* (2006.01)

(52) U.S. Cl. .................. 800/323; 800/260; 800/298

(58) Field of Classification Search ............... None
See application file for complete search history.

(56) References Cited

PUBLICATIONS

Laube et al 2008, Epiphytes of the Rio Changuinola Valley, No. 16 version 1.0, University of Oldenburg, Germany.*

* cited by examiner

*Primary Examiner* — David H Kruse
(74) *Attorney, Agent, or Firm* — Foley & Lardner LLP

(57) ABSTRACT

A new and distinct *Tillandsia leiboldiana* plant named 'MORA' characterized spreading growth habit and good vigor; funnel-form rosette, medium-sized plant, measuring about 45 cm to 50 cm in height (above the pot when flowering), and about 25 cm to 30 cm in diameter; numerous, foliage primarily green in color, and measuring about 18.5 cm in length and about 2.0 cm in width; superior floral bract production; bracts have a unique red-purple inflorescence (RHS 71A); and erect, compound inflorescence, measuring from about 35 cm in height at maturity, and about 15 cm to 20 cm in diameter.

6 Claims, 2 Drawing Sheets
(2 of 2 Drawing Sheet(s) Filed in Color)

TILLANDSIA PLANT NAMED 'MORA'

CROSS-REFERENCE TO RELATED PATENT APPLICATIONS

This application claims benefit of U.S. Provisional Application No. 61/307,663 filed Feb. 24, 2010, incorporated herein by reference in its entirety.

BACKGROUND OF THE INVENTION

The present invention relates to a new and distinct cultivar of *Tillandsia* plant, botanically known as *Tillandsia leiboldiana*, of the family Bromeliaceae, commonly referred to as air plant, Ball moss or Spanish moss, and hereinafter referred to as 'MORA'.

The present invention relates to seeds which are the *Tillandsia leiboldiana* 'MORA', as well as, plants and plant parts produced by these seeds which have all of the morphological and physiological characteristics of the *Tillandsia* 'MORA'. The present invention also relates to methods for producing these seeds and plants of the *Tillandsia leiboldiana* 'MORA'. Furthermore, the present invention relates to methods of producing progeny *Tillandsia* plants by crossing *Tillandsia leiboldiana* 'MORA', as either the female or seed or male or pollen parent, with another *Tillandsia* plant and selecting progeny.

*Tillandsia* can be found growing in the deserts, forests and mountains of Central and South America, Mexico, and southern United States. *Tillandsia* species are epiphytes, and also referred to as aerophytes. For the most part, the foliage of *Tillandsia* range in color from green to red, and thin-leaf species grow in tropical conditions whereas broad-leaf species grow in arid conditions. *Tillandsia* may be advantageously grown as potted plants for greenhouse or home use. Typically, the plants are shaded from direct sunlight.

The new *Tillandsia leiboldiana* 'MORA' originated from repeated selections of an unpatented, proprietary *Tillandsia leiboldiana* in a controlled environment in Assendelft, The Netherlands. After several selections, the new *Tillandsia leiboldiana* 'MORA' was discovered and selected by the inventors as a single flowering plant within the progeny of the stated selection in a controlled environment in 2005 in a greenhouse in Assendelft, The Netherlands. Following selection, *Tillandsia leiboldiana* 'MORA' has been under cultivation at the nursery located in Assendelft, The Netherlands.

Asexual reproduction of the new *Tillandsia leiboldiana* 'MORA' was first performed by vegetative off springs in 2005 in Assendelft, The Netherlands, with first flowering after asexual reproduction occurring in 2007 in Assendelft, The Netherlands. Asexual reproduction of *Tillandsia leiboldiana* 'MORA' has demonstrated that the combination of characteristics as herein disclosed for the new cultivar are firmly fixed and retained through successive generations of asexual reproduction. The new cultivar reproduces true-to-type by means of both asexual and sexual reproduction. Plants of the variety 'Mora' can be selfed or crossed to produce progeny plants that have the combination of characteristics herein disclosed for the new cultivar.

Methods for cultivation and crossing of *Tillandsia* are well known. For a detailed discussion, reference is made to the following publications, which are incorporated herein by reference: Benzing, David H., THE BIOLOGY OF THE BROMELIADS, Mad River Press, Inc., Eureka (1980); Zimmer, Karl, BROMELIEN Verlag, Paul Pary, Berlin (1986); and Rauh, Werner, BROMELIEN, Verlag Eugen Ulmer, Stuttgart (1981).

The new *Tillandsia leiboldiana* 'MORA' is preferably produced through seed by selfing or crossing plants of the variety 'MORA'.

This invention is directed to *Tillandsia leiboldiana* plant having all the morphological and physiological characteristics of 'MORA' produced from seeds which are the result of several selections in *Tillandsia leiboldiana*. The seed parent has a sufficient degree of homozygosis such that the progeny of the selection were, and continue to be, phenotypically uniform.

*Tillandsia leiboldiana* 'MORA' can be produced by sexual reproduction and has the combination of characteristics herein disclosed for the new variety 'MORA'.

BRIEF SUMMARY OF THE INVENTION

The following traits have been repeatedly observed and are determined to be unique characteristics of 'MORA' which in combination distinguish this *Tillandsia leiboldiana* as a new and distinct cultivar:

1. Spreading growth habit and good vigor;
2. Funnel-form rosette, medium-sized plant, measuring about 45 cm to 50 cm in height (above the pot when flowering), and about 25 cm to 30 cm in diameter;
3. Numerous, foliage primarily green in color, and measuring about 18.5 cm in length and about 2.0 cm in width;
4. Superior floral bract production;
5. Bracts have a unique red-purple inflorescence (RHS 71A); and
6. Erect, compound inflorescence, measuring from about 35 cm in height at maturity, and about 15 cm to 20 cm in diameter.

Plants of the parent, an unpatented, proprietary *Tillandsia leiboldiana*, are no longer available to provide a botanical comparison with the new *Tillandsia leiboldiana* 'MORA'. Plants of the new *Tillandsia leiboldiana* 'MORA' differ from plants of the *Tillandsia leiboldiana* parent primarily in inflorescence color and length of flowering part.

BRIEF DESCRIPTION OF THE PHOTOGRAPHS

The patent or application file contains at least one drawing executed in color. Copies of this patent or patent application publication with color drawing(s) will be provided by the Office upon request and payment of the necessary fee.

The accompanying photographs illustrate the overall appearance of the new *Tillandsia* 'MORA' showing the colors as true as is reasonably possible with colored reproductions of this type. Colors in the photographs may differ slightly from the color values cited in the detailed botanical description which accurately describes the color of 'MORA'.

SEED DEPOSIT

Figure 1:
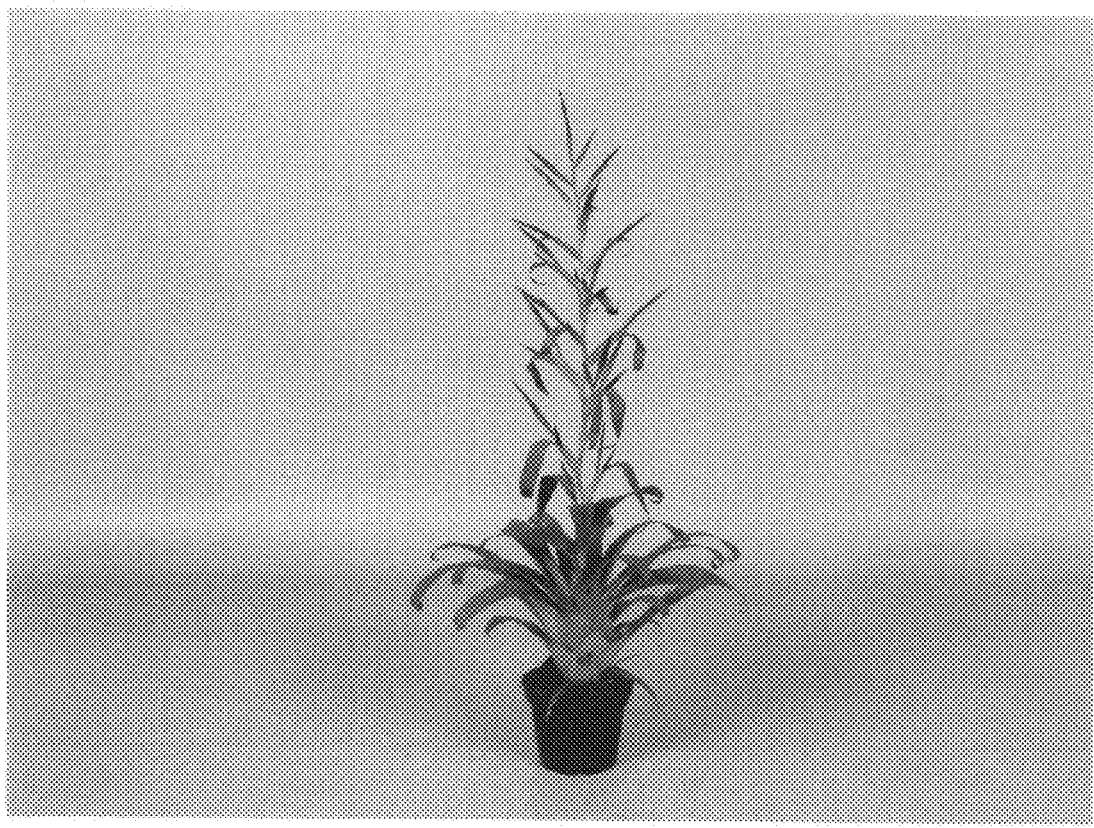
FIG. 1 shows a side view perspective of the a typical potted, flowering plant of 'MORA', at 12 months of age from potting.
Figure 2:
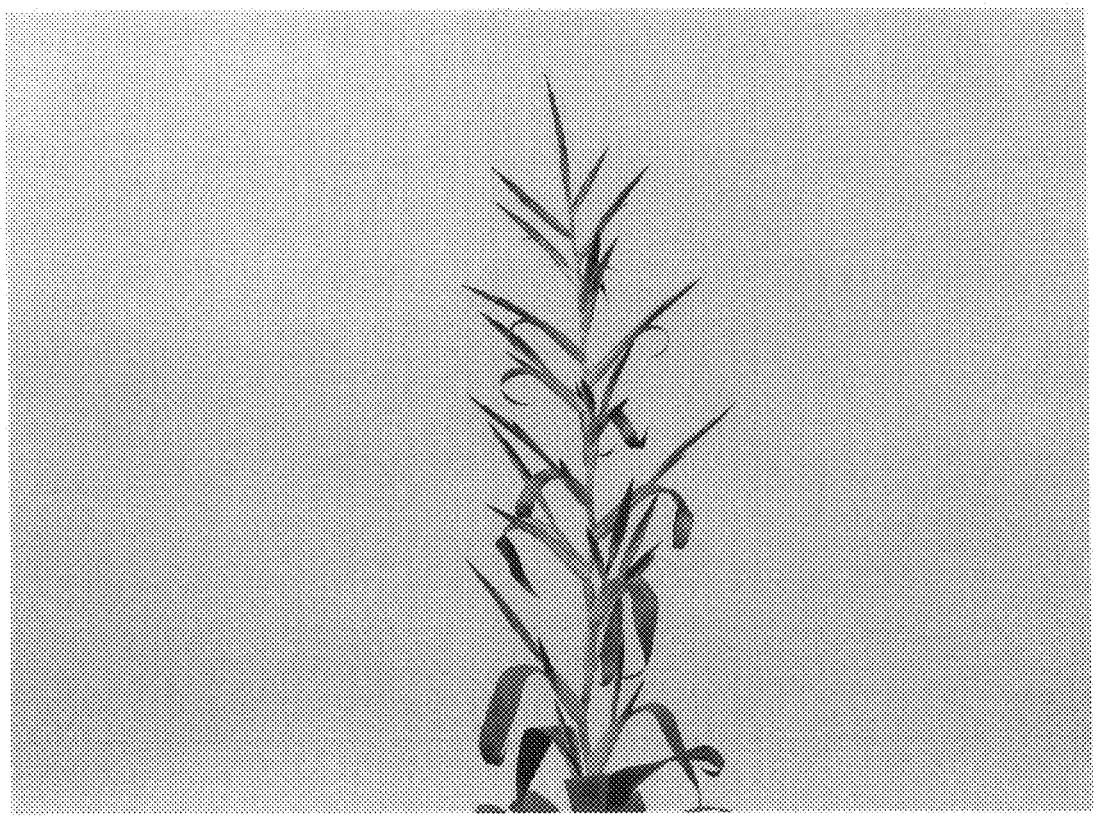
FIG. 2 shows a close-up top view perspective of the inflorescence and top bracts produced by a typical potted, flowering plant of 'MORA', 12 months of age from potting.

Seeds which are the plant *Tillandsia leiboldiana* 'MORA' are deposited under the Budapest Treaty with the recognized International Deposit Authority, the American Type Culture Collection (ATCC), 10801 University Boulevard, Manassas, Va. 20110-2209. 2500 seeds of *Tillandsia leiboldiana* 'MORA' were deposited with the ATCC on Feb. 16, 2010, and are accorded ATCC Patent Deposit Designation No PTA.-10651.

DETAILED BOTANICAL DESCRIPTION

'MORA' has not been tested and observed under all possible environmental conditions. The phenotype of the new cultivar may vary with variations in environment such as temperature, light intensity, frequency of fertilization, composition of fertilizer, flowering treatment, day length and humidity, without any change in the genotype of the plant.

For example, substantial differences in plant height and diameter, number of leaves, can result depending on the size of the plant at the time that flowering is induced by flowering treatment. Since treatment to induce flowering disrupts normal watering and fertilization regimens, flowering treatment of relatively smaller plants adversely affects the growth of the plant.

The aforementioned photographs, together with the following observations, measurements and values describe the new *Tillandsia leiboldiana* 'MORA' as grown in a greenhouse in Assendelft, The Netherlands, under conditions which closely approximate those generally used in commercial practice. Plants of 'MORA' were grown in a greenhouse with day temperatures ranging from 20° C. to 28° C. and night temperatures ranging from 18° C. to 23° C. No artificial lighting or photoperiodic treatments were conducted, but plants of 'MORA' are forced into flowering. The following fertilizer is added when growing plants of 'MORA': 1 part nitrogen, 0.6 parts phosphorus, 2 parts potassium and 0.1 parts magnesium.

Color references are made to the Royal Horticultural Society Colour Chart (RHS), 2001 edition, except where general colors of ordinary significance are used. Color values were taken under daylight conditions in a greenhouse in Assendelft, The Netherlands. The age of the plants of 'MORA' described is about 16 to 18 weeks after application of flowering treatment.

Classification:
Botanical: *Tillandsia leiboldiana*
 PARENTAGE: Unpatented, proprietary *Tillandsia leiboldiana*
 Propagation:
  Asexual: Vegetative off springs
  Sexual: Production through seed.
  Crop Time From potting, about 12 months is required to produce a finished plant.
 Plant:
  Use: Ornamental perennial.
  Growth habit: Stemless, spreading
  Plant Vigor: Good
  Plant Form Funnel form rosette
  Size (when flowering)
  Height: About 45 cm to 50 cm
  Width: About 25 cm to 30 cm
  Cold Tolerance Frost tender. Temperatures below 5° C. may damage plants.
  Fragrance: None
 Foliage:
  Quantity: About 24 (depending on the size of the plant)
  Arrangement: Overlapping, forming a rosette.
  Orientation: Leaf blades arch continuously from base
  Size of Leaf:
  Length: About 18.5 cm (when flowering)
  Width: About 2.0 cm
  Overall Shape: Linear-lanceolate
  Apex Shape: Acute
  Base Shape: Strap-like around central axis; sheathing
  Margin: Entire
  Texture (both surfaces): Smooth
  Color: Leaf color can vary somewhat depending on growing conditions
  Mature:
   Upper surface: Primarily green, RHS 137A, with red-purple anthocyanin spots, RHS 71A
   Under surface: Primarily green, RHS 137B, with red-purple anthocyanin stripes, RHS 71A
  Immature:
   Upper surface: Green, RHS 137A
   Under surface: Green, RHS 137B
  Venation pattern: Parallel
  Venation color:
  Upper surface: Green, RHS 137A
  Under surface: Green, RHS 137B
 Inflorescence:
  Borne: Erect stalks, compound inflorescence
  Size at Maturity:
  Length: About 35 cm
  Diameter: About 15 cm to 20 cm
 Flowering Season: A fully grown plant can flower year round, starting 16 to 18 weeks after induction of natural light or through flowering treatment.
 Time of Bloom: A fully grown plant can produce an inflorescence containing about 90 flowers (depending on the size of the plants), and can bloom the whole year starting about 16 to 18 weeks after natural induction or through flowering treatment.
 Duration of Bloom: Each flower blooms one (1) day and the total blooming of the whole inflorescence is about six (6) weeks.
 Flowering Habit: Continuous
 Persistent: Yes.
 Fragrance: None.
  Petals:
  Number: 3 per flower
  Length: About 3.2 cm
  Width: About 0.3 cm
  Overall Shape: Lingulate
  Apex Shape: Obtuse
  Base Shape: Fused
  Margin: Entire
  Texture:
  Upper and Under surfaces: Smooth
  Color (when fully opened):
  Upper and Under surfaces: Violet-blue, RHS 90B
  Color (when opening):
  Upper and Under surfaces: Violet-blue, RHS 90B
  Sepals:
  Number: 3 per flower
  Length: About 1.5 cm
  Width: About 0.5 cm
  Overall Shape: Linear lanceolate
  Apex Shape: Acute
  Base Shape: Fused
  Margin: Entire
  Texture:
  Upper and Under surfaces: Smooth
  Color (mature):
  Upper and Under surfaces: Violet-blue, RHS 90B
  Color (immature):
  Upper and Under surfaces: Violet-blue, RHS 90B
  Calyx:
  Overall Shape: Linear lanceolate
  Length: About 1.5 cm
  Width: About 0.5 cm
  Bracts:
  Scape Bracts:

Quantity: About 4 to 6
Arrangement: Alternate
Size:
Length: About 18 cm (lowest) to about 12 cm (scape bracts positioned just below the primary bracts).
Width: About 2.0 cm to 2.5 cm
Overall Shape: Linear, lanceolate
Apex Shape: Acute
Base Shape: Folded around the flowering stem
Margin: Entire
Texture: Smooth
Color:
   Upper surface: Green, RHS 137A
   Under surface Green, RHS 137B
Primary Bracts:
Quantity: About 20
Arrangement: Alternate
Size:
Length: About 12 cm (lowest) to about 3 cm (primary bracts become shorter closer to the top of plant)
Width: About 1.5 cm
Overall Shape: Linear, lanceolate
Apex Shape: Acute
Base Shape: Fused
Margin: Entire
Texture: Smooth
Color:
Upper surface: Red-purple, RHS 71A
Under surface: Red-purple, RHS 71A
   Floral bracts: Disposed within the inflorescence.
Quantity: About 90
Size:
Length: About 2.8 cm
Width: About 0.5 cm
Overall Shape: Linear lanceolate
Apex Shape: Acute
Base Shape: Fused
Margin: Entire
Texture: Smooth
Color:
Lower floral bracts:
   Upper and Under surfaces: Violet, RHS 86A
Higher floral bracts (closer to top of plant):
   Upper and Under surfaces: Violet, RHS 86A
Reproductive Organs:
Androecium:
Stamen:
Number: 6 per flower
Length: About 2.5 cm
Diameter: Less than 10 mm
Color: White, too small to qualify RHS value
Anther:
Length: About 2 mm
Color: White, too small to qualify RHS value
Pollen:
Amount: Moderate
Color: Too small to qualify RHS value
Gynoecium:
Pistil:
Number: 1 per flower
Length: About 4.3 cm
Stigma:
Shape: 3-parted
Width: About 0.5 mm
Color: Violet, too small to qualify RHS value
Style:
Length: About 4 cm
Color: White, too small to qualify RHS value
Ovary:
Position: Superior
Shape: Conical
Length: About 0.3 cm
Diameter: About 2 mm
Color: Light yellow, too small to qualify RHS value
Fruit:
Type: Capsule
Shape: Longitudinal
Texture: Corded
Length: About 2.5 cm
Width: About 0.5 cm
Color at maturity: Brown, RHS 199B
Seed:
Number per fruit: About 125-150 seeds (depending on the size of the plant)
Shape: Longitudinal
Texture: Plumose
Length: About 2 mm
Width: Less than 1 mm
Color at maturity: Brown, RHS 200D
DISEASE/PEST RESISTANCE: No observations made.
DISEASE/PEST SUSCEPTIBILITY: No observations made.

What is claimed is:

1. A *Tillandsia* plant named 'MORA,' obtained from seed having American Type Culture Collection (ATCC) Patent Deposit Designation No.: PTA-10651.

2. A *Tillandsia* seed deposited with the American Type Culture Collection (ATCC) under Patent Deposit Designation No.: PTA-10651.

3. A plant part obtained from the *Tillandsia* plant of claim 1.

4. A method of producing a *Tillandsia* progeny plant, comprising (a) crossing *Tillandsia* 'MORA' produced from seed accorded American Type Culture Collection (ATCC) Patent Deposit Designation No.: PTA-10651 as a female or male parent with another *Tillandsia* plant, and (b) selecting progeny.

5. The method according to claim 4, wherein said another *Tillandsia* plant is 'MORA'.

6. A method for producing a *Tillandsia* progeny plant, comprising (a) selfing a *Tillandsia* 'MORA' produced from seed accorded American Type Culture Collection (ATCC) Patent Deposit Designation No.: PTA-10651 and (b) selecting progeny.

* * * * *